United States Patent [19]

Birkofer

[11] 3,962,418

[45] June 8, 1976

[54] MILD THICKENED SHAMPOO COMPOSITIONS WITH CONDITIONING PROPERTIES

[75] Inventor: Roger Clarence Birkofer, North Bend, Ohio

[73] Assignee: The Procter & Gamble Company, Cincinnati, Ohio

[22] Filed: Apr. 8, 1975

[21] Appl. No.: 566,154

Related U.S. Application Data

[63] Continuation of Ser. No. 313,907, Dec. 11, 1972, abandoned.

[52] U.S. Cl. .................................................. 424/70
[51] Int. Cl.² ........................................ A61K 7/06
[58] Field of Search .................................... 424/70

[56] References Cited

UNITED STATES PATENTS

| | | | |
|---|---|---|---|
| 3,496,110 | 2/1970 | Shumway et al. | 424/70 |
| 3,590,122 | 6/1971 | Roberts et al. | 424/70 |

*Primary Examiner*—Sam Rosen
*Attorney, Agent, or Firm*—Robert B. Aylor; Ronald L. Hemingway; George W. Allen

[57] ABSTRACT

Mild thickened liquid shampoo compositions with conditioning properties comprise anionic surfactants, specific zwitterionic and amphoteric surfactants, polyethoxylated nonionic surfactants and a cationic cellulose ether thickening and conditioning agent.

18 Claims, No Drawings

MILD THICKENED SHAMPOO COMPOSITIONS WITH CONDITIONING PROPERTIES

CROSS-REFERENCE TO RELATED APPLICATIONS

This application is a continuation of Application Ser. No. 313,907, filed Dec. 11, 1972, now abandoned.

BACKGROUND OF THE INVENTION

1. Field of the Invention

This invention relates to thickened liquid shampoo compositions with conditioning properties, particularly those which are very mild.

2. Prior Art

Compositions containing the reaction products of ethoxylated anionic surfactants and certain specific amphoteric surfactants and polyethoxylated nonionic surfactants have been disclosed in U.S. Pat. Nos. 2,999,069 and 3,055,836, Masci and Poirier. Similar disclosures are contained in the corresponding foreign patent applications such as British Pat. Nos. 850,514, 850,515, and 921,122; and Canadian Pat. No. 595,532. In each of these patents, the disclosure is of a reaction product formed between the anionic surfactant and the amphoteric surfactant which contains ternary nitrogen groups, and there is no disclosure of thickeners.

Similarly, U.S. Pat. No. 3,580,853, Parran, discloses the cationic cellulose ether thickening and conditioning agents of this invention in shampoos to improve the deposition of particulate materials, but without a specific disclosure of the surfactant systems disclosed herein. The cationic cellulose ethers of this invention are known, having been generically disclosed in U.S. Pat. No. 3,472,840, Fred W. Stone and John M. Rutherford, Jr.

The compositions of this invention are all mild. This is a very desirable characteristic. The mildness apparently results from having a combination of anionic and cationic species present. However, as a result, many anionic, cationic, and nonionic polymers are incompatible with such formulas. It is extremely difficult to thicken such formulas and keep a single-phase clear composition. It is even more difficult to prepare a thick clear shampoo composition comprising anionic, zwitterionic or amphoteric, and nonionic surfactants which has good conditioning properties.

THE INVENTION

This invention relates to the discovery of a thickened mild liquid shampoo composition having conditioning properties comprising:

A. from about 4% to about 8% of an anionic surfactant selected from the group consisting of 1. a surfactant of the formula $R(OC_2H_4)_nOSO_3M$, wherein R is a hydrophobic group selected from the group consisting of alkyl groups containing from about 8 to about 16 carbon atoms, alkylphenyl groups wherein the alkyl group contains from about 6 to about 15 carbon atoms, and fatty acid amido groups wherein the fatty acid contains from about 8 to about 16 carbon atoms, wherein $n$ is a number from about 1 to about 10 (preferably 1 to 5) and M is a non-toxic cation which makes the surfactant water-soluble, preferably a cation selected from the group consisting of sodium, potassium, ammonium and triethanolammonium cations, (2) a water-soluble (e.g., sodium, potassium, ammonium or triethanolammonium) polyethoxylated fatty alcohol sulfosuccinate monoester wherein said fatty alcohol contains from about 8 to about 16 carbon atoms, preferably from about 10 to about 14 carbon atoms, and said polyethoxylated fatty alcohol contains from about 1 to about 10 (preferably 1 to 5) ethoxy moieties per molecule, (3) a water-soluble (e.g., sodium, potassium, ammonium, triethanolammonium, etc.) N-fatty acyl sarcosinate containing a fatty acyl group containing from about 8 to about 16 carbon atoms, (4) a water-soluble alkyl sulfate containing from about 8 to about 16 carbon atoms, and (5) a water-soluble N-fatty acyl-N-methyl taurine containing a fatty acyl group containing from about 8 to about 16 carbon atoms;

B. a surfactant selected from the group consisting of (1) a zwitterionic surfactant having the formula $$(R^2)_A N^{(+)}(R^3)_{3-A} CH_{2-B}(R^2)_B(R^4)_C Y^{(-)}$$

wherein A, B, and C are each selected from the group consisting of 0 and 1, wherein A is 0 when B is 1 and A is 1 when B is 0, wherein C can only be 1 when Y is a sulfonate group, wherein each $R^2$ is selected from the group consisting of alkyl groups containing from about 8 to about 16 carbon atoms and a moiety having the formula $R^5 - C(O)NH - R^6 -$ wherein $R^5$ is an alkyl group containing from about 8 to about 16 carbon atoms and $R^6$ is an alkylene group containing from 1 to about 5 carbon atoms (preferably 2–4 carbon atoms and most preferably 3 carbon atoms), wherein each $R^3$ is selected from the group consisting of alkyl, hydroxyalkyl and alkoxyalkyl groups which can be connected to form a ring and each of which contains from 1 to about 3 carbon atoms, wherein Y is selected from the group consisting of sulfonate and carboxylate groups, and wherein $R^4$ is an alkylene group containing from 1 to about 5 carbon atoms when Y is a carboxylate group and is selected from the group consisting of alkylene and hydroxyalkylene groups containing from about 2 to about 5 carbon atoms when Y is a sulfonate group and wherein the hydroxy group is on a secondary carbon atom, 2. a water-soluble N-alkyl β-aminopropionate wherein the alkyl group contains from about 8 to about 16 carbon atoms, and (3) a water-soluble N-alkyl β-iminodipropionate wherein the alkyl group contains from about 8 to about 16 carbon atoms;

C. a polyethoxylated nonionic surfactant selected from the group consisting of: (1) polyethoxylated alcohols, said alcohols containing an alkyl group either primary or secondary and either straight or branched chain, containing from about 8 to about 16 carbon atoms and said polyethoxylated alcohols containing from about 10 to about 45 ethoxy moieties per molecule, (2) polyethoxylated alkylphenols wherein the alkyl group contains from about 6 to about 15 carbon atoms and wherein the polyethoxylated alkylphenol contains from about 10 to about 45 ethoxy moieties per molecule, (3) polyethoxylated mono fatty acid esters of sorbitol wherein said fatty acids contain from about 8 to about 18 carbon atoms and said polyethoxylated mono fatty acid ester of sorbitol contains from about 10 to about 45 ethoxy moieties per molecule, (4) polyethoxylated polypropylene glycol having a molecular weight of from about 2,000 to about 6,000 and containing from about 40% to about 60% by weight of polyethoxy groups, and (5) polyethoxylated fatty acids wherein said fatty acid contains from about 8 to about 16 carbon atoms and said polyethoxylated fatty acid contains from about 10 to about 45 ethoxy moieties per molecule;

D. from about 50% to about 85% water; and

E. as a thickener and hair conditioning agent, from about 0.2% to about 4% (preferably from about 0.4% to about 2%) of a quaternary nitrogen-containing cellulose ether having substituent groups of the formula

wherein each $R^7$ is selected from the group consisting of methyl and ethyl groups, $m + p$ ranges from about 1 to about 10 (preferably from about 1 to about 4, most preferably from about 1 to about 2), $n$ is from about 0.1 to about 0.5, the degree of substitution of the cationic group on the cellulose is from about 0.1 to about 0.5, and the viscosity of a 1% solution of the cellulose ether at 25°C. ranges from about 100 to about 2000 centipoises, the molecular ratio of (A) to (B) being from about 1:1 to about 4:1; the weight ratio of (A) + (B) to (C) being from about 2:1 to about 1:2; and the pH of the composition being from about 6.0 to about 8.0.

DESCRIPTION OF THE INVENTION

1. The Thickener. The products of this invention are, in part, described in the copending application of Raymond Edward Bolich, Jr. and Robert Benson Aylor entitled "MILD SHAMPOO COMPOSITIONS," Ser. No. 313,908, filed Dec. 11, 1972. These compositions, and other compositions disclosed herein are very mild. However, it is very difficult to thicken such compositions while maintaining the composition in a clear, liquid single-phase form. Most anionic, cationic and nonionic polymers are incompatible with such formulas. It was discovered, however, that the quaternary nitrogen-containing cellulose ether described hereinbefore is unique in its ability to thicken the compositions of this invention while maintaining the clarity of these compositions. In addition, it has been discovered that a surprising result is obtained upon dilution of the compositions of this invention with water, as occurs during use of the shampoos. Upon dilution, an effective hair conditioning precipitate is obtained which conditions the hair to provide, e.g., superior wet-combing properties. Thus, the thickener is also a hair conditioner.

Specific thickeners are described hereinafter. Those thickeners with lower degrees of substitution of the cationic group, e.g., from about 0.15 to about 0.25, are preferred. Also preferred are those thickeners having a value of $m + p$ of about 1.5 and those thickeners whose 1% solutions have a viscosity of 125-1000 centipoises at 25°C.

2. The anionic surfactant. The polyethoxylated anionic surfactants of this invention are very mild. It is essential that the anionic surfactant be mild since it is used in a molar excess over the amount of zwitterionic surfactant present so as to minimize the amount of cationic species present. The anionic surfactant provides good lather properties. Typically, the composition will contain from about 4% to about 8% of the anionic surfactant. The sodium salts of the polyethoxylated anionic surfactants are preferred, but any non-toxic, water-soluble salt can be used, including potassium, triethanolammonium, and ammonium salts.

The preferred polyethoxylated anionic surfactants are the sodium salt of $C_{10}-C_{14}$ fatty alcohol polyethoxy(3) ether sulfate, the sodium salt of polyethoxylated(3) $C_{10}-C_{14}$ mono fatty alcohol sulfosuccinate, the sodium salt of $C_{10}-C_{14}$ fatty acyl amido polyethoxy(4) ether sulfate. Other suitable polyethoxylated anionic surfactants are disclosed hereinafter in the examples.

3. The zwitterionic surfactants. The zwitterionic surfactant provides major lather benefits while modifying the nature of the composition so that it is less strongly anionic. The molecular ratio of the anionic to zwitterionic surfactant is from about 1:1 to about 4:1, preferably from about 1:1 to about 3:1, most preferably from about 1:1 to about 2:1.

Preferred zwitterionic surfactants are propylamido betaines derived from $C_{10}-C_{16}$ fatty acids, and the corresponding propylamido sultaines, and $C_{10}-C_{16}$ alkyl sultaines wherein the cationic and sulfonate anionic groups are separated by a propylene group and the remaining groups are methyl groups. Specifically, preferred zwitterionic surfactants are (a) those having the formula

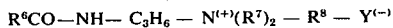

wherein $R^6$ is an alkyl group containing from about 9 to about 15 carbon atoms, wherein each $R^7$ is selected from the group consisting of methyl, ethyl, and 2-hydroxyethyl groups, wherein Y is selected from the group consisting of sulfonate and carboxylate groups, and wherein $R^8$ is a methylene group when Y is a carboxylate group and is selected from the group consisting of propylene and 2-hydroxypropylene groups when Y is a sulfonate group; and (b) those having the formula

wherein $R^9$ contains from about 10 to about 16 carbon atoms, wherein each $R^{10}$ is selected from the group consisting of methyl, ethyl, and 2-hydroxyethyl groups, and wherein X is selected from the group consisting of hydrogen and hydroxyl groups. Examples of other zwitterionic surfactants are given in the examples hereinafter.

4. The polyethoxylated nonionic surfactant. The polyethoxylated nonionic surfactant provides a mildness benefit. It also contributes to the character of the lather, although in general, the nonionic surfactant tends to control and diminish the amount of the lather. The ratio of the polyethoxylated nonionic surfactant and zwitterionic surfactant to the polyethoxylated nonionic surfactant is from about 2:1 to about 1:2, preferably from about 1:1 to about 1:2, and most preferably from about 1:1 to about 1:1.2.

Preferred nonionic surfactants include polyethoxylated (15–40) sorbitan monoacylate ($C_{10}-C_{16}$; preferably monolaurate), polyethoxylated (40–80% by weight of the molecule) polypropylene glycol (M.W. about 3–5,000), and polyethoxylated (15–40) fatty alcohols ($C_{10}-C_{14}$). Other examples of nonionic surfactants are disclosed hereinafter in the examples.

5. Water. Water is used to make up the shampoo compositions to the desired physical form. For liquid shampoos, there will normally be from about 50% to about 85% of water present, preferably from about 65% to about 80%.

6. Other ingredients. In addition to the ingredients described hereinbefore, the shampoo compositions of this invention can also contain other conventional shampoo components, including dyes, preservatives such as ethanol, perfumes, opacifiers, antibacterial agents, antidandruff agents, buffering agents, conditioning agents, etc. Desirably, only ingredients which are not irritating to the eye are added.

It is especially desirable and preferred to have buffering agents present to maintain the pH of the composition within the range from about 6.0 to about 8.0, preferably from about 6.5 to about 7.5. Such buffering agents include NaOH, HCl, NaHPO$_4$, boric acid, etc. It is also very desirable to include antidandruff agents such as zinc pyridinethiol N-oxide.

The choice of a proper thickener is complicated by the fact that the ingredients react with many anionic thickeners and many nonionic thickeners fail to thicken the compositions. The compositions of this invention can also contain another nonionic thickener, e.g., a hydroxyethyl cellulose (e.g., one with a D.S. of about 2.5 whose 1% solution has a viscosity of 3–4,000 centipoises at 25°C.). This auxilary thickener is desirable in that it also tends to provide clear, single-phase compositions.

All patents and applications referred to herein are specifically incorporated by reference.

All percentages, ratios, and parts herein are by weight unless otherwise specified.

EXAMPLE I

| Ingredient | Percent by Weight |
|---|---|
| 3-(N,N-dimethyl-N-laurylamino) propane-1-sulfonate (sultaine) | 4.5 |
| Sodium salt of sulfated polyethoxylated coconut fatty alcohol (AE$_3$S) | 7.0 |
| Polyethoxylated(20)tridecyl alcohol (β-methyl dodecanol) (PTA) | 14.0 |
| Ethanol | 7.0 |
| Cationic thickener -2 (cationic cellulose ether of Claim 7 of U.S. Pat. No. 3,472,840, wherein a is 2, b is 2, q is 0, m + p is about 1.5, n and the degree of substitution (D.S.) of the cationic group are about 0.2, and the viscosity of a 1% solution is 125–1000 centipoises at 25°C.) | 1.25 |
| Water | balance |
| pH adjusted to 7.0 with HCl | |

EXAMPLE II

| Ingredient | Percent by Weight |
|---|---|
| N-(3-coconutacylamidopropyl)-N,N-di(2-hydroxyethyl)-3-aminopropane-sulfonate | 5.0 |
| Sodium salt of sulfated polyethoxylated(4) lauroylamide (ethoxylated amido sulfate) | 8.0 |
| Tween 20 | 13.0 |
| Natrosol 250 HH [A hydroxyethyl cellulose (D.P. — 2.5) having a viscosity at 1% in water at 25°C of 3–4,000 centipoises] | 0.5 |
| Cationic thickener -2 | 0.5 |
| Ethanol | 7.0 |
| Water | balance |
| Adjusted to pH of 7.0 with NaH$_2$PO$_3$ | |

EXAMPLE III

| Ingredient | Percent by Weight |
|---|---|
| Sultaine | 4.00 |
| AE$_3$S | 5.50 |
| Polyethoxylated(50%)polypropyleneglycol (molecular weight 3,000) (PPG) | 14.00 |
| Cationic thickener -2 | .60 |
| Ethanol | 7.00 |
| Perfume | 0.25 |
| Distilled water | balance |
| Adjusted pH to 7.0 with HCl. | |

EXAMPLE IV

| Ingredient | Percent by weight |
|---|---|
| N-(3-coconutacylamidopropyl)-N,N-dimethyl-2-aminoacetate (Amido betaine) | 3.00 |
| Sodium polyethoxylated(3)lauryl sulfosuccinate (Ethoxylated sulfosuccinate) | 7.00 |
| Polyethoxylated(20)sorbitol monolaurate (Tween 20) | 15.00 |
| Cationic thickener -2 | 0.50 |
| Ethanol | 7.00 |
| Distilled water | balance |
| Adjusted pH to 7.0 with NaOH. | |

EXAMPLE V

| Ingredient | Percent by Weight |
|---|---|
| 3-[N-undecyl-N-ethyl-N-(2-hydroxyethyl) ammonio]-butyrate | 4.5 |
| Potassium polyethoxylated(3) tridecanolether sulfate | 6.6 |
| Polyethoxylated(30)sorbitol monococonutacylate | 17.0 |
| Ethanol | 6.0 |
| Cationic thickener -1 (same as thickener of Example I except having a D.S. of the cationic group of 0.4 and a viscosity at 25°C. with a 1% solution of about 1,500–3,000) | 1.0 |
| Water | balance |
| Adjusted pH to 7.0 with HCl. | |

EXAMPLE VI

| Ingredient | Percent by Weight |
|---|---|
| AE$_3$S | 6.50 |
| Tween 20 | 14.0 |
| Amido betaine | 5.00 |
| Cationic thickener -1 | 1.00 |
| Water | balance |

EXAMPLE VII

| Ingredient | Percent by Weight |
|---|---|
| Sultaine | 4.90 |
| AE$_3$S | 6.60 |
| Tween 20 | 14.0 |
| Cationic thickener -2 | 0.50 |
| Ethanol | 7.00 |
| Water | balance |

EXAMPLE VIII

| Ingredient | Percent by Weight |
|---|---|
| Amido betaine | 4.00 |
| Ethoxylated sulfosuccinate | 8.15 |
| PTA | 14.00 |
| Ethanol | 7.00 |
| Cationic thickener -2 | 0.48 |
| Na$_3$HPO$_4$.12H$_2$O | 0.65 |
| NaH$_2$PO$_4$.H$_2$O | 0.35 |
| Water | balance |

EXAMPLE IX

| Ingredient | Percent by Weight |
|---|---|
| Amido betaine | 5.00 |
| AE$_3$S | 7.15 |
| PTA | 14.00 |
| Cationic thickener -1 | 0.50 |
| Water | balance |

EXAMPLE X

| Ingredient | Percent by Weight |
|---|---|
| Sultaine | 4.90 |
| AE$_3$S | 6.60 |
| PTA | 14.00 |
| Ethanol | 7.00 |
| Cationic thickener -1 | 0.50 |
| Water | balance |

EXAMPLE XI

| Ingredient | Percent by Weight |
|---|---|
| Amido betaine | 4.00 |
| Ethoxylated sulfosuccinate | 8.15 |
| PTA | 14.00 |
| Ethanol | 7.00 |
| Cationic thickener -1 | 0.50 |
| Water | balance |

EXAMPLE XII

| Ingredient | Percent by Weight |
|---|---|
| Sultaine | 4.50 |
| AE$_3$S | 7.00 |
| PTA | 14.00 |
| Ethanol | 7.00 |
| Cationic thickener -2 | 0.46 |
| Water | balance |

EXAMPLE XIII

| Ingredient | Percent by Weight |
|---|---|
| Amido betaine | 4.00 |
| Ethoxylated sulfosuccinate | 8.15 |
| Tween 20 | 14.00 |
| Ethanol | 7.00 |
| Cationic thickener -2 | 0.46 |
| Water | balance |

EXAMPLE XIV

| Ingredient | Percent by Weight |
|---|---|
| Sodium N-alkyl(C$_{12}$;C$_{14}$) β-aminopropionate | 4.00 |
| AE$_3$S | 6.70 |
| Tween 20 | 14.00 |
| Ethanol | 7.00 |
| Cationic thickener -2 | 0.50 |
| Water | balance |

EXAMPLE XV

| Ingredient | Percent by Weight |
|---|---|
| Sultaine | 4.50 |
| AE$_3$S | 7.00 |
| Tween 20 | 14.00 |
| Ethanol | 7.00 |
| Natrosol 250 HH | 0.30 |
| Cationic thickener -2 | 0.30 |
| Water | balance |

EXAMPLE XVI

| Ingredient | Percent by Weight |
|---|---|
| Sultaine | 5.00 |
| Sodium N-coconut acyl-N-methyl taurate | 5.50 |
| PTA | 14.00 |
| Cationic thickener -2 | 0.50 |
| Distilled water | balance |

EXAMPLE XVII

| Ingredient | Percent by Weight |
|---|---|

| Ingredient | Percent by Weight |
|---|---|
| C-cetyl betaine | 4.00 |
| AE₃S | 7.50 |
| Tween 20 | 14.00 |
| Cationic thickener -2 | 0.50 |
| Water | balance |

EXAMPLE XVIII

| Ingredient | Percent by Weight |
|---|---|
| Amido betaine | 5.40 |
| Na N-lauroyl sarcosinate | 5.20 |
| PTA | 14.00 |
| Cationic thickener -2 | 0.50 |
| Distilled water | balance |

EXAMPLE XIX

| Ingredient | Percent by Weight |
|---|---|
| Amido betaine | 5.00 |
| Sodium coconut alkyl sulfate | 6.00 |
| Tween 20 | 14.00 |
| Cationic thickener -2 | 0.50 |
| Distilled water | balance |

When in the above Examples I–XIX the following zwitterionic surfactants are substituted for the specifically named zwitterionic surfactants, substantially equivalent results are obtained in that the shampoos are exceptionally mild to the eyes.

1. 4-[N-coconutacylamidopropylene-N,N-di(2-hydroxypropyl)-ammonio]butane-1-sulfonate;
2. 2[N-pentadecylamidopropylene-N-(3-hydroxypropyl)-N-propylammonio]ethane-1-sulfonate;
3. 4(N-laurylmorpholino)2-hydroxybutanoate;
4. 3-(N-laurylmorpholino)propane-1-sulfonate;
5. 3-(N-tridecyl-N-methyl-N-propyl)-aminopropanoate;
6. 4-(N,N,N-trimethylammonio)stearate;
7. 3-[N-methyl-N-(2-hydroxyethyl)-N-propylammonio]eicosane-1-sulfonate;
8. 5-[N,N-(3-hydroxypropyl)-N-methylammonio]-3-hydroxydocosane-1-carboxylate;
9. N-coconutalkyl betaine;
10. C-cetyl betaine;
11. C-hexadecyl betaine;
12. 3-(N,N-dimethyl-N-coconutalkylammonio)-2-hydroxypropane-1-sulfonate;
13. 6-coconutacylamido-3-trimethylammoniohexanoate;
14. 7-coconutacylamido-4-tri(2-hydroxyethyl)-heptane-1-sulfonate;
15. 3-[N-(3-coconutacylamidopropyl)-N,N-dimethylammonio]-propane-1-sulfonate;
16. 3-[N-(3-coconutacylamidopropyl)-N,N-di(2-hydroxyethyl)ammonio]-2-hydroxypropane-1-sulfonate;
17. 6-(N-coconutalkyl-N,N-dimethyl)hexanoate;
18. 5-(N,N-dipropyl-N-dodecylammonio)pentane-1-sulfonate;
19. 3-(N-methylmorpholino)stearate;
20. Potassium N-coconutalkyl β-aminopropionate;
21. Ammonium N-coconutalkyl β-iminodipropionate.

When in the above Examples I–XIX, the following ethoxylated anionic surfactants are substituted for the specifically named ethoxylated anionic surfactants, either totally or in part (e.g., a 1:1 ratio), substantially equivalent results are obtained in that the shampoos are exceptionally mild to the eyes:

1. Ammonium polyethoxylated(10)octanol ether sulfate;
2. Triethanolammonium polyethoxylated(2)2-ethyltetradecanol sulfate;
3. Potassium polyethoxylated(4) octylphenol ether sulfate;
4. Sodium polyethoxylated(6)pentadecylphenol ether sulfate;
5. Diethanolammonium polyethoxylated(4)dodecane-2-ol ether sulfate;
6. Monoethanolammonium polyethoxylated(5)tetrapropylene phenol ether sulfate;
7. Sodium polyethoxylated(8)3-nonylphenol ether sulfate;
8. Potassium polyethoxylated(4)octoylamide ether sulfate;
9. Triethanolammonium polyethoxylated(5)hexadecoylamide ether sulfate;
10. Potassium polyethoxylated(2)octanol sulfosuccinate monoester;
11. Triethanolammonium polyethoxylated(10)hexadecanol sulfosuccinate monoester;
12. Potassium N-coconutacyl sarcosinate.

When in the above Examples I–XIX, the following ethoxylated nonionic surfactants are substituted for the specifically named ethoxylated nonionic surfactants, either totally or in part (e.g., a 1:1 ratio), substantially equivalent results are obtained in that the shampoos are exceptionally mild to the eyes:

1. Polyethoxylated(40)octanol;
2. Polyethoxylated(10)hexadecanol;
3. Polyethoxylated(25)2-ethylnonanol;
4. Polyethoxylated(18)dodecane-2-ol;
5. Polyethoxylated(35)hexylphenol;
6. Polyethoxylated(30)pentadecylphenol;
7. Polyethoxylated(40)tetrapropylenephenol;
8. Polyethoxylated(25)3-nonylphenol;
9. Polyethoxylated(35)sorbitan monostearate;
10. Polyethoxylated(25)sorbitan monooctanoate;
11. Polyethoxylated(25)polypropylene glycol (M.W. 1000);
12. Polyethoxylated(25)octanoate;
13. Polyethoxylated(30)hexadecanoate.

What is claimed is:

1. A thickened mild liquid shampoo composition having conditioning properties comprising:
   A. from about 4% to about 8% of an anionic surfactant selected from the group consisting of (1) a surfactant of the formula $R(OC_2H_4)_nOSO_3M$, wherein R is a hydrophobic group selected from the group consisting of alkyl groups containing from about 8 to about 16 carbon atoms, alkylphenyl groups wherein the alkyl group contains from about 6 to about 15 carbon atoms, and fatty acid amido groups wherein the fatty acid contains from about 8 to about 16 carbon atoms, wherein $n$ is a number from about 1 to about 10, and M is a non-toxic cation which makes the surfactant water-soluble, (2) a water-soluble polyethoxylated fatty alcohol sulfosuccinate monoester, (3) a water-soluble N-fatty acyl sarcosinate containing a fatty acyl group containing from about 8 to about 16 carbon atoms, (4) a water-soluble alkyl sulfate containing from about 8 to about 16 carbon atoms, and (5) a water-soluble N-fatty acyl-N-methyl taurine containing a fatty acyl group containing from about 8 to about 16 carbon atoms;

B. a surfactant selected from the group consisting of (1) a quaternary ammonium zwitterionic surfactant having the formula $(R^2)_A N^{(+)}(R^3)_{3-A} CH_{2-B}(R^2)_B(R^4)_C Y^{(-)}$
wherein A, B, and C are each selected from the group consisting of 0 and 1, wherein A is 0 when B is 1 and A is 1 when B is 0, wherein C can only be 1 when Y is a sulfonate group, wherein each $R^2$ is selected from the group consisting of alkyl groups containing from about 8 to about 16 carbon atoms and a moiety having the formula $R^5 - C(O)NH - R^6-$ wherein $R^5$ is an alkyl group containing from about 8 to about 16 carbon atoms and $R^6$ is an alkylene group containing from 1 to about 5 carbon atoms, wherein each $R^3$ is selected from the group consisting of alkyl, hydroxyalkyl and alkoxyalkyl groups which can be connected to form a ring and each of which contains from 1 to about 3 carbon atoms, wherein Y is selected from the group consisting of sulfonate and carboxylate groups, and wherein $R^4$ is an alkylene group containing from 1 to about 5 carbon atoms when Y is a carboxylate group and is selected from the group consisting of alkylene and hydroxyalkylene groups containing from about 2 to about 5 carbon atoms when Y is a sulfonate group and wherein the hydroxy group is on a secondary carbon atom, and (2) a water-soluble N-alkyl β-aminopropionate wherein the alkyl group contains from about 8 to about 16 carbon atoms, and (3) a water-soluble N-alkyl β-iminodipropionate wherein the alkyl group contains from about 8 to about 16 carbon atoms;

C. a polyethoxylated nonionic surfactant selected from the group consisting of: (1) polyethoxylated alkyl alcohols, said alcohols containing an alkyl group containing from about 8 to about 16 carbon atoms and said polyethoxylated alcohols containing from about 10 to about 45 ethoxy moieties per molecule, (2) polyethoxylated alkylphenols wherein the alkyl group contains from about 6 to about 15 carbon atoms and wherein the polyethoxylated alkylphenol contains from about 10 to about 45 ethoxy moieties per molecule, (3) polyethoxylated mono fatty acid esters of sorbitol wherein said fatty acids contain from about 8 to about 18 carbon atoms and said polyethoxylated mono fatty acid ester of sorbitol contains from about 10 to about 45 ethoxy moieties per molecule, (4) polyethoxylated polypropylene glycol having a molecular weight of from about 2,000 to about 6,000 and containing from about 40% to about 60% by weight of polyethoxy groups, and (5) polyethoxylated fatty acids wherein said fatty acid contains from about 8 to about 16 carbon atoms and said polyethoxylated fatty acid contains from about 10 to about 45 ethoxy moieties per molecule;

D. from about 50% to about 85% water; and

E. as a thickener and hair conditioning agent, from about 0.2% to about 4% of a quaternary nitrogen-containing cellulose ether having substituent groups of the formula $(C_2H_4O-)_m[-CH_2CHO(CH_2N^{(+)}(R^7)_3Cl^{(-)})-]_n(C_2H_4O-)_pH$ wherein each $R^7$ is selected from the group consisting of methyl and ethyl groups, $m + p$ ranges from about 1 to about 10, $n$ is from about 0.1 to about 0.5, the degree of substitution of the cationic group on the cellulose is from about 0.1 to about 0.5, and the viscosity of a 1% solution of the cellulose ether at 25°C. ranges from about 100 to about 2,000 centipoises, the molecular ratio of (A) to (B) being from about 1:1 to about 4:1; the weight ratio of (A) + (B) to (C) being from about 2:1 to about 1:2; and the pH of the composition being from about 6.0 to about 8.0.

2. The composition of claim 1 wherein the quaternary nitrogen containing cellulose ether has a degree of substitution of the cationic group of from about 0.15 to about 0.25.

3. The composition of claim 1 wherein $m + p$ has a value of about 1.5.

4. The composition of claim 1 wherein the viscosity of a 1% solution of component E at 25°C. is from about 125–1000 centipoises.

5. The composition of claim 1 wherein the molecular ratio of the anionic surfactant to the zwitterionic surfactant is from about 1:1 to about 3:1.

6. The composition of claim 5 wherein the molecular ratio of the anionic surfactant to the zwitterionic surfactant is from about 1:1 to about 2:1.

7. The composition of claim 1 having a pH of about 7.0.

8. The composition of claim 1 wherein the zwitterionic surfactant has the formula $R^6 CO-NH - C_3H_6 - N^{(+)}(R^7)_2 - R^8 - Y^{(-)}$ wherein $R^6$ is an alkyl group containing from about 9 to about 15 carbon atoms, wherein each $R^7$ is selected from the group consisting of methyl, ethyl, and 2-hydroxyethyl groups, wherein Y is selected from the group consisting of sulfonate and carboxylate groups, and wherein $R^8$ is a methylene group when Y is a carboxylate group and is selected from the group consisting of propylene and 2-hydroxypropylene groups when Y is a sulfonate group.

9. The composition of claim 6 wherein Y is a carboxylate group.

10. The composition of claim 6 wherein Y is a sulfonate group.

11. The composition of claim 1 wherein the zwitterionic surfactant has the formula $R^9 N^{(+)}(R^{10})_2 CH_2CHX CH_2SO_3^{(-)}$ wherein $R^9$ contains from about 10 to about 16 carbon atoms, wherein each $R^{10}$ is selected from the group consisting of methyl, ethyl, and 2-hydroxyethyl groups, and wherein X is selected from the group consisting of hydrogen and hydroxyl groups.

12. The composition of claim 1 wherein the anionic surfactant is a sodium salt of a fatty alcohol polyethoxy ether sulfate containing a fatty alkyl group containing from about 10 to about 14 carbon atoms and about 3 ethoxy moieties per molecule.

13. The composition of claim 1 wherein the anionic surfactant is a sodium salt of a polyethoxylated fatty alcohol sulfosuccinate monoester wherein the polyethoxylated fatty alcohol contains about 3 ethoxy moieties per molecule and a fatty alcohol moiety containing from about 10 to about 14 carbon atoms.

14. The composition of claim 1 wherein R is a fatty acid amido group containing from about 10 to about 14 carbon atoms and $n$ is about 3.

15. The composition of claim 1 wherein the nonionic surfactant is a polyethoxylated mono fatty acid ester of sorbitol wherein the fatty acid contains from about 10 to about 16 carbon atoms and wherein there are from about 15 to about 40 ethoxy moieties per molecule.

16. The composition of claim 1 wherein the nonionic surfactant is a polyethoxylated fatty alcohol wherein said fatty alcohol contains from about 10 to about 14 carbon atoms and wherein there are from about 15 to about 40 ethoxy moieties per molecule.

17. The composition of claim 1 wherein the nonionic surfactant is a polyethoxylated polypropylene glycol wherein said polypropylene glycol has a molecular weight of from about 2000 to about 6000 and contains from about 40% to about 60% by weight of polyethoxy groups.

18. The composition of claim 1 wherein the anionic surfactant contains a cation selected from the group consisting of sodium, potassium, ammonium, and triethanolammonium cations.

* * * * *